(12) United States Patent
Grubbs et al.

(10) Patent No.: US 12,343,455 B2
(45) Date of Patent: Jul. 1, 2025

(54) PHOTOCATALYTIC GENERATION OF SINGLET OXYGEN FOR AIR PURIFICATION

(71) Applicant: California Institute of Technology, Pasadena, CA (US)

(72) Inventors: Robert H. Grubbs, South Pasadena, CA (US); Carl M. Blumenfeld, West Hills, CA (US); Harry B. Gray, Pasadena, CA (US); George R. Rossman, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 269 days.

(21) Appl. No.: 17/524,654

(22) Filed: Nov. 11, 2021

(65) Prior Publication Data

US 2022/0211894 A1 Jul. 7, 2022

Related U.S. Application Data

(60) Provisional application No. 63/112,732, filed on Nov. 12, 2020.

(51) Int. Cl.
*A61L 9/015* (2006.01)
*A61L 2/20* (2006.01)
(Continued)

(52) U.S. Cl.
CPC ............... *A61L 9/015* (2013.01); *A61L 2/20* (2013.01); *B01J 27/132* (2013.01); *B01J 31/16* (2013.01);
(Continued)

(58) Field of Classification Search
CPC ........ A61L 9/015; A61L 2/20; A61L 2101/02; A61L 2202/11; A61L 2202/15;
(Continued)

(56) References Cited

U.S. PATENT DOCUMENTS 10,520,435 B2 12/2019 Ghosh et al.
2015/0330899 A1 11/2015 Vasdekis et al.
(Continued)

FOREIGN PATENT DOCUMENTS

JP 2010/057908 A 3/2010
JP 5700859 B2 4/2015
(Continued)

OTHER PUBLICATIONS

Riehl et al , "A ligand substituted tungsten iodide cluster: luminescent vs. singlet oxygen production", Dalton Trans., 2016, 45, 15500-15506. (Year: 2016).*
(Continued)

*Primary Examiner* — Xiuyu Tai
(74) *Attorney, Agent, or Firm* — Leydig, Voit & Mayer, Ltd.

(57) ABSTRACT

Aspects disclosed herein include a system for generating singlet oxygen in a gas, the system comprising: a substrate; and hexanuclear clusters operably immobilized on at least a portion of the substrate; wherein each hexanuclear cluster comprises a photosensitive octahedral core complex characterized by formula FX1a: $M_6X_8$ (FX1a); wherein each M is independently Mo, W, or Re; wherein each X is independently a halide anion ligand; wherein the clusters are exposed to the gas and the gas comprises $O_2$ gas; wherein the clusters are exposed to a light; and wherein each hexanuclear cluster is a photosensitizer configured to generate the gaseous singlet oxygen when irradiated by the light in the presence of the $O_2$ gas.

21 Claims, 9 Drawing Sheets

(51) Int. Cl.
    B01J 27/132    (2006.01)
    B01J 31/16     (2006.01)
    B01J 35/39     (2024.01)
    C01B 13/02     (2006.01)
    A61L 101/02    (2006.01)

(52) U.S. Cl.
    CPC .............. *B01J 35/39* (2024.01); *C01B 13/02* (2013.01); *A61L 2101/02* (2020.08); *A61L 2202/11* (2013.01); *A61L 2202/15* (2013.01); *A61L 2209/16* (2013.01); *A61L 2209/21* (2013.01); *B01J 2531/64* (2013.01)

(58) Field of Classification Search
    CPC .... A61L 2209/16; A61L 2209/21; A61L 9/18; A61L 2209/12; A61L 9/205; A61L 9/01; B01J 35/39; B01J 27/132; B01J 31/16; B01J 2531/64; B01J 2219/0875; B01J 2219/0892; B01J 19/127; B01J 31/0202; B01J 35/00; B01J 35/30; B01J 35/51; B01J 31/06; B01J 31/0208; B01J 31/0232; B01J 37/0009; B01J 37/344; B01J 2231/005; B01J 2231/70; B01J 2531/002; C01B 13/02; A61M 15/02; A61M 2202/0275; A61M 2202/0007; B01D 53/8678; B01D 2255/802; B01D 2255/70; B01D 53/38; B01D 53/8603; B01D 53/8606; B01D 2257/306; B01D 2251/102; C08G 63/52; C08G 63/91; C09B 11/24; C09B 67/0092; C09B 67/0097; C08F 283/01; C08F 210/10; C08L 2666/70; C08L 67/06
    See application file for complete search history.

(56) References Cited

U.S. PATENT DOCUMENTS

| | | |
|---|---|---|
| 2017/0216348 A1 | 8/2017 | Goodson, III et al. |
| 2018/0099063 A1 | 4/2018 | Lyons et al. |

FOREIGN PATENT DOCUMENTS

| | | | |
|---|---|---|---|
| RU | 2692371 C1 | 6/2019 | |
| WO | WO 03/106583 A1 | 12/2003 | |
| WO | WO-2012056225 A1 * | 5/2012 | ............ B01J 19/127 |

OTHER PUBLICATIONS

Baker et al. (2003) "Fiber Optical Micro-detectors for Oxygen Sensing in Power Plants," Quarterly Technical Progress Report, Reporting Period: Oct. 1, 2002 to Dec. 31, 2002, DOE Award No. DE-FC26-02NT41582, 13 pp.
Bartusik et al. (2012) "Bacterial inactivation by a singlet oxygen bubbler: identifying factors controlling the toxicity of $^1O_2$ bubbles," Environ Sci Technol. 46(21):12098-12104. doi:10.1021/es303645n.
Bartusik et al. (2012) "Generating singlet oxygen bubbles: a new mechanism for gas-liquid oxidations in water," Langmuir. 28(5):3053-3060. doi:10.1021/la204583v.
Beltrán et al. (2016) "Photobleaching resistant polymer supported hexanuclear molybdenum iodide cluster for photocatalytic oxygenations and photodynamic inactivation of *Staphylococcus aureus*," J. Mater. Chem. B, 4, 5975-5979.
Davies (2003) "Singlet oxygen-mediated damage to proteins and its consequences," Biochemical and Biophysical Research Communications 305, 761-770.
Gelest, Inc. (2014) "Silane Coupling Agents: Connecting Across Boundaries," 3rd Edition, Barry Arkles, 76 pp.
Ghosh et al. (1999) "Fiber-optic oxygen sensor using molybdenum chloride cluster luminescence," Applied Physics Letters, 75, 19, 2885-2887.
International Search Report and Written Opinion dated Mar. 3, 2022 in corresponding International Application No. PCT/US2021/059020, 11 pp.
Ionin et al. (2007) "Physics and engineering of singlet delta oxygen production in low-temperature plasma," J. Phys. D: Appl. Phys. 40, R25-R61.
Jackson et al. (1990) "Oxygen Quenching of Electrontcally Excited Hexanuclear Mdybdenum and Tungsten Halide Clusters," J. Phys. Chem. 94, 4500-4507.
Jarvi et al. (2012) "Insights into photodynamic therapy dosimetry: Simultaneous singlet oxygen luminescence and photosensitizer photobleaching measurements," Biophys J. 102(3):661-671. doi:10.1016/j.bpj.2011.12.043.
Jockusch et al. (2008) "Singlet molecular oxygen by direct excitation," Photochem. Photobiol. Sci., 7, 235-239.
Kim et al. (Aug. 2020) "Photosensitized Production of Singlet Oxygen via $C_{60}$ Fullerene Covalently Attached to Functionalized Silica-coated Stainless-Steel Mesh: Remote Bacterial and Viral Inactivation," Applied Catalysis B: Environmental, 270, 118862.
Kirakci et al. (Nov. 2020) "Electrophoretically Deposited Layers of Octahedral Molybdenum Cluster Complexes: A Promising Coating for Mitigation of Pathogenic Bacterial Biofilms under Blue Light." ACS Appl. Mater. & Interfaces, 12 (47), 52492-52499.
Kraut et al. (1989) "Photochemical Reactivity of the Cluster $Mo_6Cl_{14}^{2-}$: Photosubstitution and Photoredox Processes," Inorganic Chemistry, vol. 28, No. 26, 4578-4583.
Levi et al. (May 2021) "Redox Potential and Crystal Chemistry of Hexanuclear Cluster Compounds," Molecules, 26, 3069.
Maisch et al. (2007) "The role of singlet oxygen and oxygen concentration in photodynamic inactivation of bacteria," PNAS, 104, 17, 7223-7228.
Maisch et al. (2014) "Fast and Effective Photodynamic Inactivation of Multiresistant Bacteria by Cationic Riboflavin Derivatives," PLOS One. 9(12):e111792. doi:10.1371/journal.pone.0111792.
Maverick (1982) "Spectroscopy and Photochemistry of Polynuclear Metal Complexes," Dissertation (Ph.D.), California Institute of Technology. doi:10.7907/PBEA-8W62.
Maverick et al. (1983) "Spectroscopic, Electrochemical, and Photochemical Properties of Molybdenum( 11) and Tungsten( 11) Halide Clusters," J. Am. Chem. Soc., 105, 7, 1878-1882.
Nocera (1984) "Spectroscopy, Electrochemistry, and Photochemistry of Polynuclear Metal-Metal Bonded Complexes," Dissertation (Ph.D.), California Institute of Technology. doi:10.7907/T14G-4N32.
Ogilby et al. (1983) "Chemistry of singlet oxygen. 42. Effect of solvent, solvent isotopic substitution, and temperature on the lifetime of singlet molecular oxygen (1.Delta.g)" J. Am. Chem. Soc. 105, 11, 3423-3430.
Silindir et al. (2009) "Sterilization Methods and the Comparison of E-Beam Sterilization with Gamma Radiation Sterilization," Fabad J Pharm Sci. 34, 43-53.
Sousa (2008) "Singlet Oxygen Reactivity in Water-Rich Solvent Mixtures," Quim. Nova, vol. 31, No. 6, 1392-139.
Ströbele et al. (2009) "The Synthesis and Luminescence of $W_6Cl_{12}$ and $Mo_6Cl_{12}$ Revisited," Zeitschrift fur Anorg und Allg Chemie, 635, 822-827.
Sunday et al. (Dec. 2020) "A simple, inexpensive method for gas-phase singlet oxygen generation from sensitizer-impregnated filters: Potential application to bacteria/virus inactivation and pollutant degradation," Sci Total Environ. 746: 141186.
Svezhentseva et al. (2017) "Water-soluble hybrid materials based on $\{Mo_6X_8\}^{4+}$ (X=Cl, Br, I) cluster complexes and sodium polystyrene sulfonate," New J. Chem., 41, 1670.
Urata et al. (2003) "Comparison of the Microbicidal Activities of Superoxidized and Ozonated Water in the Disinfection of Endoscopes," J Int Med Res. 31:299-306.
Vorotnikov et al. (2016) "On the synthesis and characterisation of luminescent hybrid particles: $Mo_6$ metal cluster complex/$SiO_2$," RSC Adv., 6, 43367.

(56) References Cited

OTHER PUBLICATIONS

Vorotnikova et al. (Aug. 2019) "Octahedral molybdenum cluster as a photoactive antimicrobial additive to a fluoroplastic," Materials Science and Engineering: C, 105, 110150.
Wasserman et al. (2013) "Singlet Oxygen," Encyclopedia of Reagents for Organic Synthesis (EROS), 11 pp.
Winston (2008) "Mechanisms of Singlet Oxygen Reactions," Stoltz Research Group.
Zamadar et al. (2009) "Singlet Oxygen Delivery Through the Porous Cap of a Hollow-Core Fiber Optic Device," J. Phys. Chem. B, 113, 15803-15806.
Zhao (2001) "Singlet Oxygen," Department of Radiology, The University of Iowa, 10 pp.
DeRosa et al. (2002) "Photosensitized singlet oxygen and its applications," Coord Chem Rev. 233-234, 351-371. doi:10.1016/S0010-8545(02)00034-6.
Felip-León et al. (2017) "Superior performance of macroporous over gel type polystyrene as a support for the development of photo-bactericidal materials." J. Mater. Chem. B, 5, 6058-6064.
Jackson et al. (1996) "Efficient Singlet Oxygen Generation from Polymers Derivatized with Hexanuclear Molybdenum Clusters", Chem. Mater. 8, 558-564, DOI: 10.1021/cm950443f.
Muñoz-Castro et al. (Apr. 2019) "Rhenium Hexanuclear Clusters: Bonding, Spectroscopy, and Applications of Molecular Chevrel Phases," Ligated Transition Metal Clusters in Solid-state Chemistry pp. 109-123, Cite as Chapter, First Online: Apr. 28, 2019, Part of the Structure and Bonding book series (Structure, vol. 180).
Vorotnikova et al. (May 2021) "Heterogeneous photoactive antimicrobial coatings based on a fluoroplastic doped with an octahedral molybdenum cluster compound," Dalton Trans., 50, 8467-8475.

\* cited by examiner

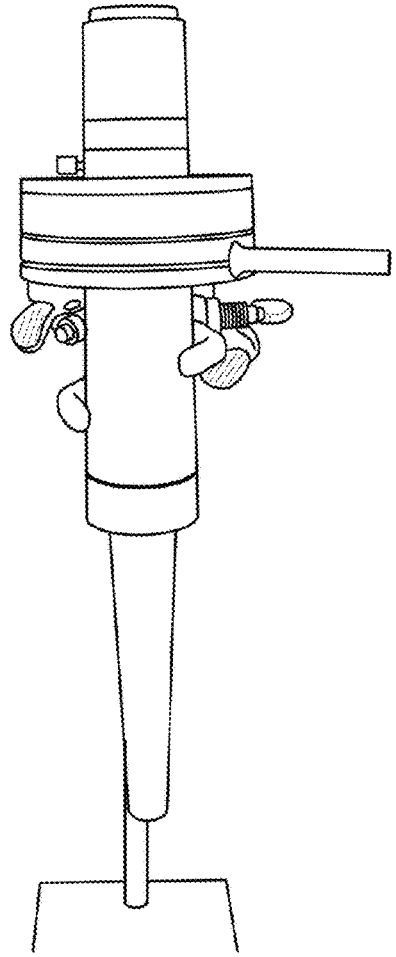
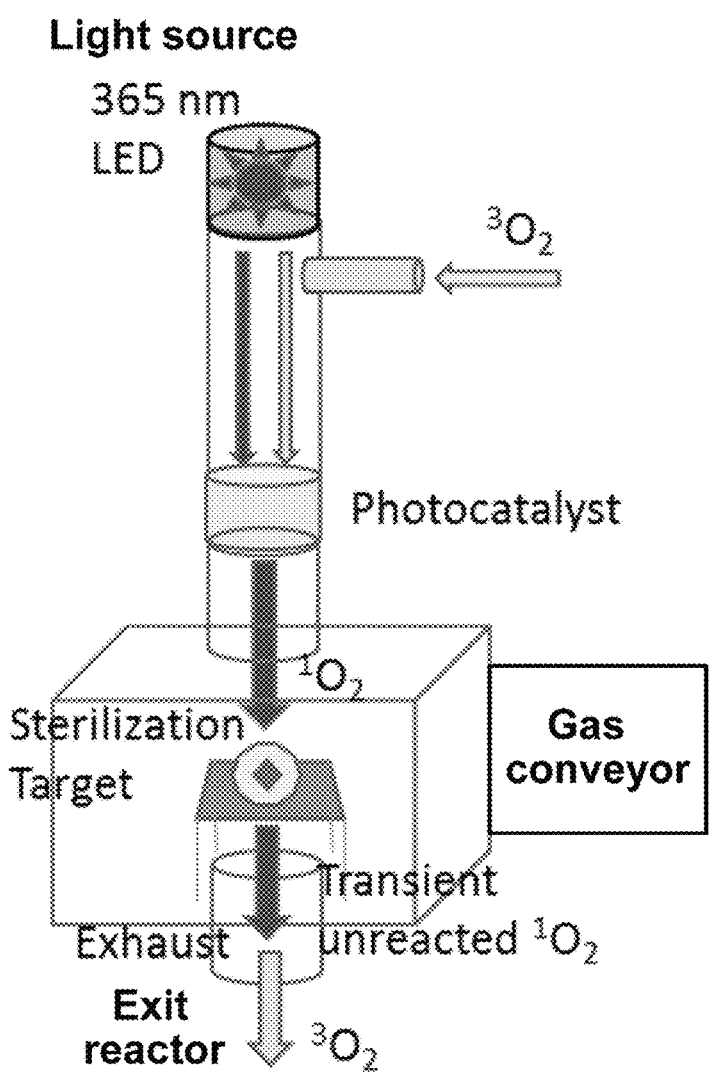
FIG. 3A
FIG. 3B ns for and priority to U.S.

PHOTOCATALYTIC GENERATION OF SINGLET OXYGEN FOR AIR PURIFICATION

CROSS-REFERENCE TO RELATED APPLICATIONS

This application claims the benefit of and priority to U.S. Provisional Patent Application No. 63/112,732, filed Nov. 12, 2020, which is hereby incorporated by reference in its entirety.

BACKGROUND OF INVENTION

In its ground state or un-energized, with two unpaired electrons, molecular oxygen ($O_2$) is in a triplet state. Notably, oxygen can be excited into a more energetic state, referred to as singlet oxygen. Singlet oxygen has been employed in the treatment of diseases including various types of cancer in a process referred to as photodynamic therapy (PDT). In PDT, a photosensitizer in mammalian tissue is exposed to light and oxygen. The photosensitizer is excited and subsequently energizes the oxygen from the triplet ground state to the excited singlet state. The reactive singlet oxygen then causes irreversible oxidative damage to malignant tissues.

Singlet oxygen has been explored as a tool for killing multi-resistant bacteria. Examples in the literature include the inactivation of MRSA (Methicillin resistant *Staphylococcus aureus*), EHEC (enterohemorrhagic *Escherichia coli*), *Pseudomonas aeruginosa*, and *Acinetobacter baumannii*. Studies have demonstrated that photodynamic inactivation of bacteria was effective and independent of bacterial type and existing resistance pattern. Singlet oxygen has demonstrated efficacy against in the viruses in air. Singlet oxygen non-selectively oxidizes cell components. Thus, photodynamic therapy or inactivation is not expected to promote bacterial resistance, making it a powerful option against viruses, bacteria, and fungi as a whole, especially where traditional methods of sterilization have failed. Oxygen and light are the two reagents required for this technology.

Photogeneration of singlet oxygen was developed during the last century, but the methods are expensive, cumbersome, and dangerous. Many photosensitizers can be employed, but they are subject to bleaching or destruction by way of reaction with the very singlet oxygen they generate. For example, photosensitizing nanoparticles have been generated for use in a device to generate singlet oxygen in water, but the materials are expensive and wasteful. Organic photosensitizers, on the other hand, are subject to degradation by singlet oxygen and photobleaching. As such, before singlet oxygen can become a viable tool in the purification sector, its generation must become cost effective by using materials that are inexpensive to manufacture, are effective photosensitizers for generating singlet oxygen, and are robust and stable for long periods of time.

SUMMARY OF THE INVENTION

Included herein are systems and methods that provide effective photosensitizers for generating singlet oxygen that are robust and stable for long periods, e.g., years. The systems and methods disclosed herein include hexanuclear clusters as photosensitizers for generating singlet oxygen. The hexanuclear clusters comprise a photosensitive octahedral core complex. The systems and methods may be used to generate singlet oxygen for inactivation of airborne pathogens and/or inactivation of pathogens on surfaces. Applications of these systems and methods include a portable or non-portable system for cleaning or sterilizing air in a medical facility, such as for provide a sterile air curtain or providing a local sterile environment. Applications more generally include a room air circulation system, an air filtration system, a medical facility air cleaning system, a clean-room air cleaning system, a utensil disinfection system, or any combination of these. The systems disclosed herein may be permanent systems or portable gas disinfection systems. They may be standalone systems or integrated with other gas circulation systems, such as residential or commercial large-volume air circulation systems.

Aspects disclosed herein include a system for generating singlet oxygen in a gas, the system comprising: a substrate; and hexanuclear clusters operably immobilized on at least a portion of the substrate; wherein each hexanuclear cluster comprises a photosensitive octahedral core complex characterized by formula FX1a: $M_6X_8$ (FX1a); wherein each M is independently Mo, W, or Re; wherein each X is independently a halide anion ligand; wherein the clusters are exposed to the gas and the gas comprises $O_2$ gas; wherein the clusters are exposed to a light; and wherein each hexanuclear cluster is a photosensitizer configured to generate the gaseous singlet oxygen when irradiated by the light in the presence of the $O_2$ gas. Preferably for some applications, each M is independently Mo or W.

Aspects disclosed herein include a system for inactivation of pathogens via singlet oxygen, the system comprising: a photosensitizing component for generating gaseous singlet oxygen, comprising: a substrate; and hexanuclear clusters operably immobilized on the substrate; wherein each hexanuclear cluster comprises a photosensitive octahedral core complex characterized by formula FX1a: $M_6X_8$ (FX1a); wherein each M is independently Mo, W, or Re; and wherein each X is independently a halide anion; a conveyed gas in gas-communication with the photosensitizing component; wherein the clusters are exposed to the gas and the gas comprises $O_2$ gas; a light source configured to emit a light onto the hexanuclear clusters, the light being capable of photoactivating the hexanuclear clusters; wherein each hexanuclear cluster is a photosensitizer configured to generate the gaseous singlet oxygen when irradiated by the light in the presence of the $O_2$ gas. A photosensitizing component is optionally a volume, a compartment, a vessel, a chamber, a tube, a port, a portion of any of these, or the like. Preferably for some applications, each M is independently Mo or W.

Optionally, any system disclosed herein is a system for inactivation of airborne pathogens, wherein: the conveyed gas comprises the airborne pathogens to inactivate the airborne pathogens in the gas via the gaseous singlet oxygen. Optionally, any system disclosed herein is a system for inactivation of pathogens on a surface, wherein: the conveyed gas, having the generated gaseous singlet oxygen, flows from the photosensitizing component onto the surface; and the conveyed gas comprises the generated gaseous singlet oxygen at the surface.

The systems and methods disclosed herein are compatible with hexanuclear clusters of a variety of compositional variations. Optionally, in any system and method disclosed herein, the core complex is characterized by formula FX1b or FX1c: $Mo_6X_a$ (FX1b); or $Mo_6Cl_8$ (FX1c). Optionally, in any system and method disclosed herein, each hexanuclear cluster is independently neutral, cationic, or anionic; wherein each cationic cluster, if present, is charge-balanced with one or more counterions; and wherein each anionic cluster, if present, is charge-balanced with one or more counterions. Optionally, in any system and method disclosed herein, each of the hexanuclear clusters is independently characterized by formula FX2a, FX2b, or FX2c: $M_6X_8L_6$ (FX2a); $M_6X_8L_4$ (FX2b); or $M_6X_8L_2$ (FX2c); wherein: each M is independently Mo or W; each X is independently a halide anion ligand; and each L is independently an organic or inorganic monoanion ligand. Optionally, in any system and method disclosed herein, each X is the same halide anion as each other X. Optionally, in any system and method disclosed herein, each L is independently an inorganic monoanion. Optionally, in any system and method disclosed herein, each L is independently a halide monoanion. Optionally, in any system and method disclosed herein, each L is independently Cl, Br, or I. Optionally, in any system and method disclosed herein, each L is independently Cl, Br, I, C, or O. Optionally, in any system and method disclosed herein, each L is independently Cl, Br, I, C, O, N or S. Optionally, in any system and method disclosed herein, each of the hexanuclear clusters is independently characterized by formula FX2d, FX2e, or FX2f: $M_6X_8(L')^{6+}$ (FX2d); $M_6X_8(L')^{4+}$ (FX2e); or $M_6X_8(L')^{2+}$ (FX2f); wherein: each M is independently Mo or W; each X is independently a halide anion ligand; and each L' is independently one or more organic or inorganic monoanion and/or polyanion ligands. Optionally, in any system and method disclosed herein, each of at least a fraction of the hexanuclear clusters is independently a compound characterized by formula FX2a, FX2b, or FX2c: $(M_6X_8L_6)^{2-}(A^C)_p^{2+}$ (FX3a); $(M_6X_8L_4)(A^N)_n$ (FX3b); or $(M_6X_8L_2)^{2+}(A^A)_m^{2-}$ (FX3c); wherein: each M is independently Mo or W; each X is independently a halide anion ligand; each L is independently an organic or inorganic monoanion; p is 2 and each $A^C$ is independently a counterion being an organic or inorganic monocation or p is 1 and $A^C$ is a counterion being an organic or inorganic dication; m is 2 and each $A^A$ is independently a counterion being an organic or inorganic monoanion or m is 1 and $A^A$ is a counterion being an organic or inorganic dianion; and n is an integer selected from the range of 1 to 2 and $A^N$ is an organic or inorganic neutral Lewis base ligand. Optionally, n is an integer selected from the range of 1 to 5. Optionally, in any system and method disclosed herein, each L is independently an inorganic monoanion. Optionally, in any system and method disclosed herein, each L is independently a halide monoanion. Optionally, in any system and method disclosed herein, each L is independently Cl, Br, or I. Optionally, in any system and method disclosed herein, each $A^N$ may independently be, but is not limited to, N, a substituted or unsubstituted pyridine, a substituted or unsubstituted amine, a substituted or unsubstituted methide, carbon monoxide, a substituted or unsubstituted triphenylphosphine, a substituted or unsubstituted triphenylarsine, a substituted or unsubstituted dimethylsulfide, a substituted or unsubstituted diemthylselenide, ammonia, and any combination thereof. Optionally, in any system and method disclosed herein, each $A^N$ is independently selected from the group consisting of N, a substituted or unsubstituted pyridine, a substituted or unsubstituted amine, a substituted or unsubstituted methide, carbon monoxide, a substituted or unsubstituted triphenylphosphine, a substituted or unsubstituted triphenylarsine, a substituted or unsubstituted dimethylsulfide, a substituted or unsubstituted diemthylselenide, ammonia, and any combination thereof. Optionally, in any system and method disclosed herein, each $A^C$ is independently selected from the group consisting of a metal monocation, $NH^{4+}$, tetrabutylammonium, tetramethylammonium, tetraethylammonium, organic dications, alkaline earth metal dications, and any combination thereof. Optionally, in any system and method disclosed herein, each $A^C$ may independently be, but is not limited to, a metal monocation, $NH^{4+}$, tetrabutylammonium, tetramethylammonium, tetraethylammonium, organic dications, alkaline earth metal dications, and any combination thereof. Optionally, in any system and method disclosed herein, each of the hexanuclear clusters comprises a composition characterized by formula FX4: $M_6X_{12}$ (FX4); each M is independently Mo or W; and each X is independently a halide anion. Optionally, in any system and method disclosed herein, each X is Cl, Br, or I. Optionally, in any system and method disclosed herein, each M is Mo or W and each X is Cl, Br, or I. Optionally, in any system and method disclosed herein, each M is Mo and each X is Cl. The hexanuclear clusters disclosed herein may optionally include or be chemically associated with neutral species, which are not necessarily represented by the formulas, such as in the case of the clusters being hydrated.

Optionally, in any system and method disclosed herein, the substrate has a composition characterized as a metal oxide, a nonmetal oxide, a metalloid oxide, a polymer, a coordination polymer or polymeric material, an organofluoride material, an allotrope of carbon, or a combination of these. Optionally, in any system and method disclosed herein, the substrate comprises a plurality of carbon-fluoride bonds. Optionally, in any system and method disclosed herein, the substrate fluoropolymer and/or a perfluorinated substance. Optionally, in any system and method disclosed herein, the portion of the substrate having the clusters operably immobilized thereon has a porosity sufficient to be permeable by $O_2$ gas. Optionally, in any system and method disclosed herein, the substrate comprises a mesh, filter, a powder, a compressed-powder, or a membrane that is permeable to $O_2$ gas.

Optionally, in any system and method disclosed herein, the substrate comprises metal oxide or non-metal oxide particles having the clusters operably connected or associated thereto. Optionally, in any system and method disclosed herein, at least a fraction of the hexanuclear clusters are non-covalently attached to the substrate. Optionally, in any system and method disclosed herein, at least a fraction of the hexanuclear clusters are covalently attached to the substrate. Optionally, in any system and method disclosed herein, at least a fraction of the hexanuclear clusters are covalently attached to a portion of the substrate having a metal oxide or nonmetal oxide composition via a silane compound or silane group. Optionally, in any system and method disclosed herein, at least a fraction of the hexanuclear clusters are covalently attached to a portion of the substrate that is a polymer. Optionally, in any system and method disclosed herein, at least a fraction of the hexanuclear clusters are covalently attached to the substrate accordingly to formula FX10a, FX10b, FX10c, FX10d, FX10e, or FX10f:

$$[S^{mo,nmo}]-Z^1-Z^2-[(M_6X_8L_6)] \quad \text{(FX10a)}$$

$$[S^{mo,nmo}]-Z^1-Z^3-[(M_6X_8L_4)] \quad \text{(FX10b)}$$

$$[S^{mo,nmo}]-Z^1-Z^4-[(M_6X_8L_2)] \quad \text{(FX10c)}$$

$$[S^{pol}]-Z^5-[(M_6X_8L_6)] \quad \text{(FX10d)}$$

$$[S^{pol}]-Z^6-[(M_6X_8L_4)] \quad \text{(FX10e); or}$$

$[S^{pol}]-Z^7-[(M_6X_8L_2)]$ (FX10f); wherein: $S^{mo,nmo}$ is a portion of the substrate having a composition characterized as a metal oxide or a non-metal oxide; $S^{pol}$ is a portion of the substrate that is a polymer; $Z^1$ is a silane compound or silane group; each of $Z^2$ and $Z^5$ is an organic cation; each of $Z^3$ and $Z^6$ is a neutral ligand compound; each of $Z^4$ and $Z^7$ is an anion; each L is independently an organic or inorganic monoanion ligand; each M is independently Mo or W; and each X is independently a halide anion. Optionally, in any system and method disclosed herein, each L is independently an inorganic monoanion. Optionally, in any system and method disclosed herein, each L is independently a halide monoanion. Optionally, in any system and method disclosed herein, each L is independently Cl, Br, or I.

Optionally, in any system and method disclosed herein, the light source is a lamp or lamp array, an LED or LED array, laser or laser array, and/or solar irradiation. The light source is a source of photons.

Optionally, in any system and method disclosed herein, the system or method comprises a gas handling component, such as a gas conveyor, including one or more fans, one or more blowers, one or more compressors, one or more pumps, one or more fluid actuators or a combination of these for conveying the gas to or near the clusters and/or from the clusters. Optionally, in any system and method disclosed herein, the gas is air, for example, air from an enclosure. In an embodiment, the gas handling component generates a flow of gas through the system, for example, a turbulent flow of gas capable of bringing pathogens in the air in contact with singlet oxygen generated by the hexanuclear clusters.

Optionally, in any system and method disclosed herein, the immobilized clusters are characterized by a quantum yield for singlet oxygen generation of at least 80% at a wavelength of the visible portion of the light.

Optionally, in any system and method disclosed herein, the system is integrated with an HVAC system, a room air circulation system, an air filtration system, a medical facility air cleaning system, a clean-room air cleaning system, a utensil disinfection system, or any combination of these. For example, useful applications include utilizing systems and methods disclosed herein to form an air curtain for surgery or to form a sterile environment. Optionally, in any system and method disclosed herein, the system is a standalone permanent or portable gas disinfection system; or wherein the system is operably integrated with or operably connected to another gas circulation system. The system optionally expels singlet oxygen such as in the case of the system being used to create a stream or curtain of singlet oxygen for sterile environments.

Aspects disclosed herein include a method for generating gaseous singlet oxygen in a gas, the method comprising: exposing hexanuclear clusters to a gas comprising $O_2$ gas; and irradiating the hexanuclear clusters with a light (optionally for some embodiments, a light comprising visible light; and optionally for some embodiments a light comprising visible light, ultraviolet light, near infrared light, or any combination of these); wherein: each hexanuclear cluster is a photosensitizer generating gaseous singlet oxygen when irradiated by the light in the presence of the $O_2$ gas the hexanuclear clusters are operably immobilized on at least a portion of a substrate; each hexanuclear cluster comprises a photosensitive octahedral core complex characterized by formula FX1a: $M_6X_8$ (FX1a); each M is independently Mo, W, or Re; and each X is independently a halide anion. Preferably for some applications, each M is independently Mo or W. Optionally, the method is a method for inactivating airborne pathogens in the gas, wherein the method comprises: conveying the gas, having the airborne pathogens, to the hexanuclear clusters; inactivating the airborne pathogens in the gas via exposure of the airborne pathogens to the generated gaseous singlet oxygen; and removing gas having inactivated airborne pathogens away from the clusters. Optionally, the method is a method for inactivating pathogens on a surface, wherein the method comprises: conveying gas having the generated gaseous singlet oxygen from the hexanuclear clusters to the surface; and inactivating the pathogens on the surface via exposure of the pathogens to the generated gaseous singlet oxygen. Optionally, the method comprises generating the singlet oxygen in: a cleanroom, a manufacturing facility, a medical facility, a residential or commercial air circulation system, or any combination of these. Optionally, the method comprises inactivating the pathogens in: a cleanroom, a manufacturing facility, a medical facility, a residential or commercial air circulation system, or any combination of these.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 3: A photograph (FIG. 3A; left) of an example system for generating singlet oxygen, according to aspects herein. In certain embodiments, the device is configured to direct or convey gas comprising singlet oxygen onto a surface for inactivating pathogens on or near the surface. In certain embodiments, the device is configured to inactivate airborne pathogens. Also shown is a schematic (FIG. 3B; right) of a system for generating singlet oxygen, according to aspects herein. In embodiments, the depicted system may be used for inactivation of airborne pathogens, in which features shown downstream of the photocatalysts, such as the sterilization target and exit reactor, may be optional. Embodiments disclosed herein include variations of the systems depicted here.

6 utilize, for example, a silane linker molecule or silane group; however, a wide range of chemistries are useable for immobilization of hexanuclear clusters on substrates, including covalent association and non-covalent association.

Figure 7:
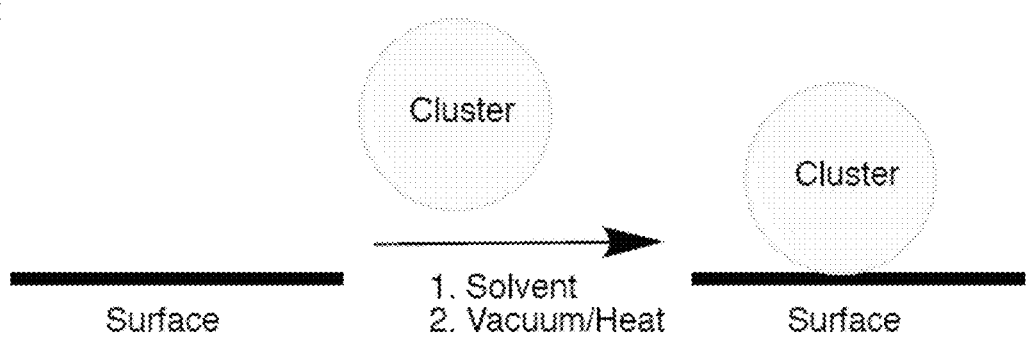

FIG. 7: Exemplary schematic depicting non-covalent immobilization, according to various aspects herein, of hexanuclear clusters, according to various aspects herein, on a surface of a substrate. The schematic shows immobilization of the clusters via adsorption to a surface.

Figure 8:
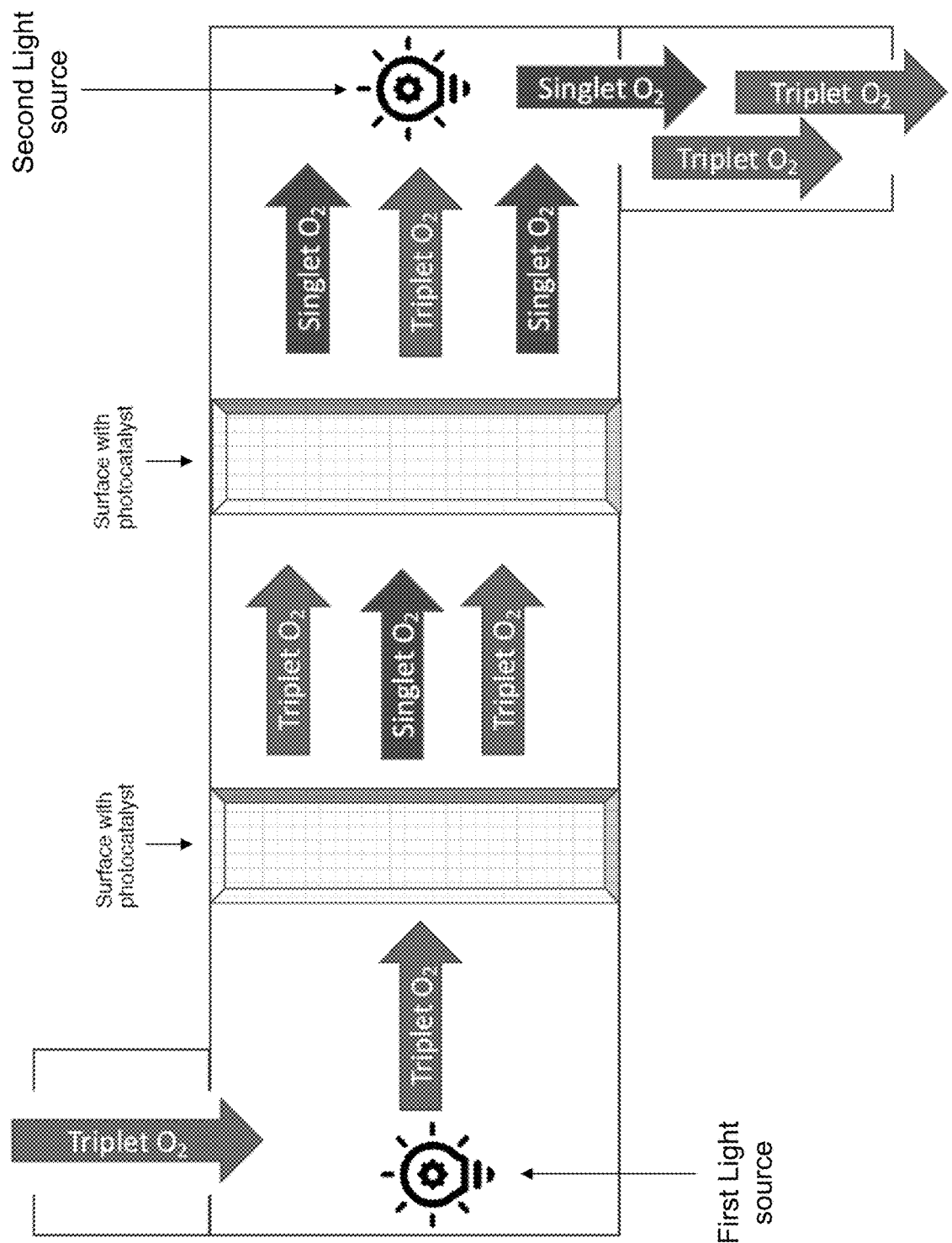

FIG. 8: A schematic depicting an example system for generating singlet oxygen, according to various aspects disclosed herein.

Figure 9:
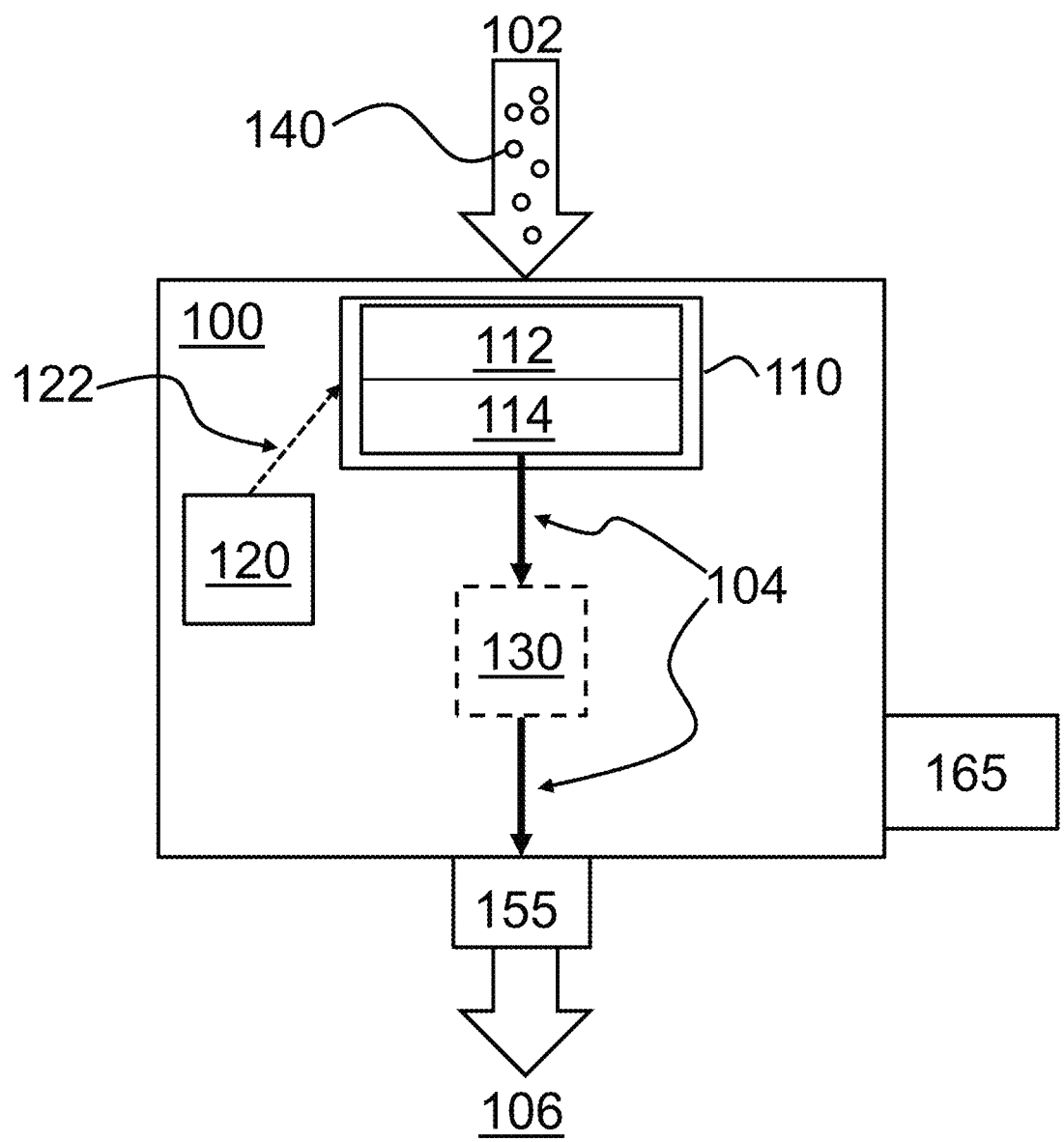

FIG. 9: A schematic depicting an example system for generating singlet oxygen, according to various aspects disclosed herein.

STATEMENTS REGARDING CHEMICAL COMPOUNDS AND NOMENCLATURE

In general, the terms and phrases used herein have their art-recognized meaning, which can be found by reference to standard texts, journal references and contexts known to those skilled in the art. The following definitions are provided to clarify their specific use in the context of the invention.

The term "hexanuclear cluster" may also be referred to as a hexanuclear metal cluster complex or hexanuclear metal cluster compound and is intended to be consistent with these terms as would be recognized by one of skill in the fields of materials science and inorganic chemistry. The term "hexanuclear cluster" refers a metal cluster complex having exactly six metal atoms interacting with each other via metal-metal bonds. In general, a metal cluster complex is an atom cluster that is a molecular ion or neutral compound having three or more metal atoms or metal ions (six metal in the case of a hexanuclear cluster) and having metal-metal interactions among the metal atoms or metal ions of the cluster. As used herein, a hexanuclear cluster may be an anion, a cation, or a neutral compound. A hexanuclear cluster include metal-metal interactions among the metal atoms of the cluster and further includes monoatomic and/or polyatomic ligands coordinated with or bound to the metal atoms of the cluster. Ligands of a hexanuclear cluster may include, for example, halide ions. For example, a hexanuclear complex may be characterized by formula FX5: $Mo_6Cl_{12}$. A neutral hexanuclear cluster may include one or more neutral Lewis base ligands, such as pyridine, coordinated with the cluster. An ionic hexanuclear cluster is generally charge-balanced by one or more counterions that are coordinated with and/or ionically associated with the cluster. A counterion may be monoatomic or polyatomic. A counterion may be a ligand. Hexanuclear clusters described herein comprise a photosensitive octahedral core complex, characterized by formula FX1a: $M_6X_8$, wherein each M is independently a transition metal atom, such as Mo, W, or Re, and wherein each X is independently a halide anion ligand. Preferably for some applications, each M is independently Mo or W. An octahedral core complex refers to the core or inner complex (or, optionally, sub-complex) of the hexanuclear cluster where the structural arrangement of the six metal atoms may be characterized as octahedral. The eight (8) ligands X of the octahedral core complex may also be referred to as inner ligands of the hexanuclear complex and are bound with the metal atoms of the hexanuclear cluster. Hexanuclear clusters disclosed herein are photosensitive and are capable of being photosensitizers. Aspects of the hexanuclear clusters relevant to embodiments disclosed herein are also described in the following literature, all of which is incorporated herein by reference in their entirety, to the extent not inconsistent herewith: (1) D. Nocera, "Spectroscopy, Electrochemistry, and Photochemistry of Polynuclear Metal-Metal Bonded Complexes" 1984, Thesis, California Institute of Technology, DOI: 10.7907/T14G-4N32; (2); B. Kraut, et al., "Photochemical reactivity of the cluster tetradecachlorohexamolybdate(2-): photosubstitution and photoredox processes", Inorg. Chem. 1989, 28, 26, 4578-4583, DOI: 10.1021/ic00325a009; (3) A. W. Maverick, et al., "Spectroscopic, electrochemical, and photochemical properties of molybdenum(II) and tungsten(II) halide clusters", J. Am. Chem. Soc. 1983, 105, 7, 1878-1882, DOI: 10.1021/ja00345a034; (4) J. A. Jackson, et al., "Efficient Singlet Oxygen Generation from Polymers Derivatized with Hexanuclear Molybdenum Clusters", Chem. Mater. 1996, 8, 558-564, DOI: 10.1021/cm950443f; (6) J. A. Jackson, et al., "Oxygen quenching of electronically excited hexanuclear molybdenum and tungsten halide clusters", *J. Phys. Chem.* 1990, 94, 11, 4500-4507, DOI: 10.1021/j100374a029; (7) R. N. Ghosh, et al., "Fiber-optic oxygen sensor using molybdenum chloride cluster luminescence", Appl. Phys. Lett. 75, 2885 (1999), DOI 10.1063/1.125180; and (8) E. Levi, et al., "Redox Potential and Crystal Chemistry of Hexanuclear Cluster Compounds", Molecules, 26, 2021, DOI: 10.3390/molecules26113069.

Figure 2:
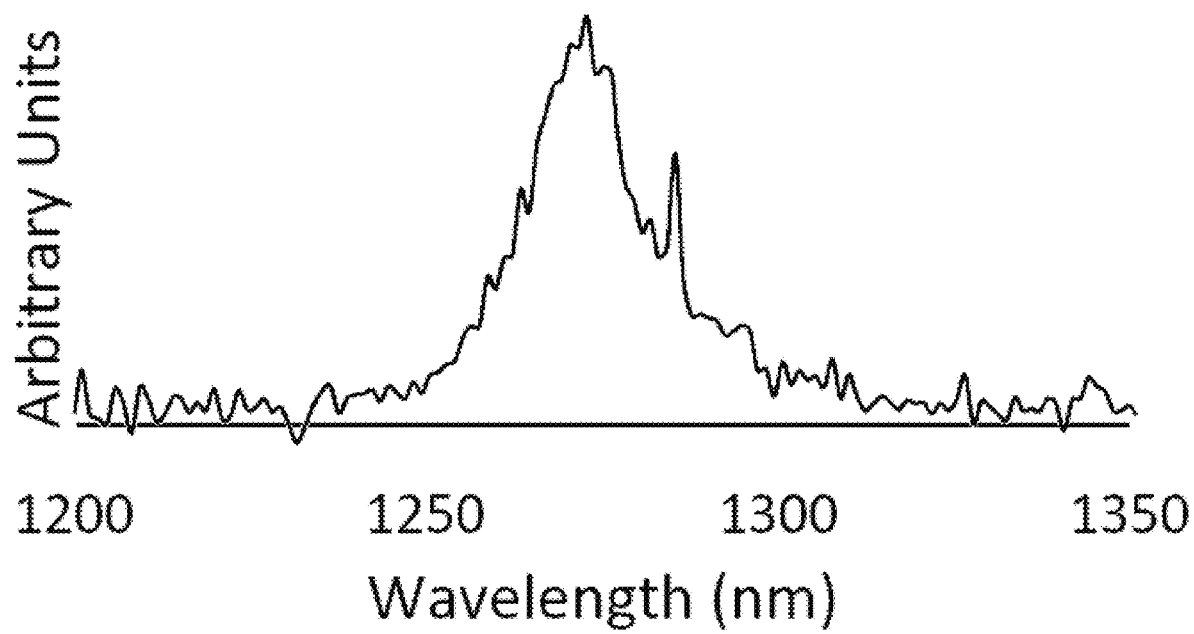
FIG. 2: Example singlet oxygen emission spectrum (wavelength (nm) vs. intensity (arbitrary units)) from hexanuclear clusters, according to embodiments disclosed herein, in solution.

The term "photosensitive" refers to a compound, such as a hexanuclear cluster, or a portion thereof, such as an octahedral core complex, that is capable of being photoexcited via light, or energy transfer from photons. Without wishing to be bound by any particular theory, a photoexcited cluster exists in an electronically excited state or form for some short duration of time. The photoexcited cluster may return to ground state by emission of one or more photons, corresponding to luminescence of the clusters. The photoexcited cluster may return to ground state by transfer of energy to another molecule or compound, such as a triplet or ground-state oxygen molecule. A photosensitizer is a photosensitive compound or molecule that is capable of absorbing light energy and then transferring at least a portion of the absorbed energy to another, nearby, molecule or compound. FIG. 2 provides an example singlet oxygen emission spectrum from hexanuclear clusters, according to embodiments disclosed herein, in solution.

The term "triplet oxygen" refers to the electronic ground state of molecular or diatomic oxygen (dioxygen) and is represented in the art as "$^3O_2$". The term "singlet oxygen" refers to an excited electronic state of molecular or diatomic oxygen (dioxygen) in which all electron are spin paired, also referred to in the art as "dioxygen(singlet)" and "dioxidene" and is represented in the art as "$^1O_2$" or "$^1[O_2]$". As used herein, singlet oxygen is a gaseous molecule, rather than a condensed or liquid molecule. As used herein "$O_2$ gas" refers to gaseous molecular oxygen ($O_2(g)$) and is understood to comprise gaseous triplet oxygen, singlet oxygen, or a combination of these.

A cluster "immobilized" on a substrate refers to a cluster that is chemically and/or physically bound to, attached to, or affixed to the substrate or a surface thereof. An "operably immobilized" is an immobilized cluster that is capable of performing the intended function when immobilized, wherein the intended function is for example that of being a photosensitizer for generating singlet oxygen. In preferred embodiments, operably immobilized hexanuclear clusters are capable of and configured to being irradiated by a light, absorbing said light, being in the presence of or exposed to a gas comprising triplet oxygen, and generating singlet oxygen by photosensitizing triplet oxygen in the gas. An immobilized cluster may be covalently attached and/or non-covalently attached to a substrate, or surface thereof. A cluster may be non-covalently attached to a substrate by, for example, van der Waals forces, hydrogen bonding, ionic interaction, and/or other non-covalent interaction(s). A cluster may be non-covalently attached to a substrate directly or indirectly, such as by being non-covalently attached to a chemical species that is itself covalently or non-covalently or non-covalently attached to the substrate. A cluster may be covalently attached to a substrate directly or indirectly, such as via a covalent linker atom or group. In some aspects, a region of a substrate having hexanuclear clusters comprises more than a monolayer (e.g., bilayer or more layers) of the hexanuclear clusters. In such regions, the second layer, or a subsequent layer, may be attached to the prior or neighboring layer of hexanuclear clusters rather than necessarily to the underlying substrate. The attachment of hexanuclear clusters to neighboring hexanuclear clusters may involve covalent attachment, non-covalent attachment (e.g., an ionic interaction and/or van der Waals), or a combination of these.

The term "pathogen" is intended to be consistent with the term as would be recognized by one of skill in the fields of biology and medicine. A pathogen broadly refers to a microorganism or infectious agent capable of causing disease in a living organism, human, plant, or animal. Exemplary pathogens include, but are not limited to, bacteria, viruses, protozoa, prions, viroids, and fungi. An "airborne" pathogen is a pathogen that is suspended in a gas, such as air.

The term "inactivation" refers to inactivation of a pathogen and is intended to be consistent with the meaning of pathogen inactivation as would be recognized by one of skill in the fields of biology and medicine. Inactivation broadly refers to rendering a pathogen inactive or incapable of infection or causing a disease in a living subject.

As used herein, the term "monoanion" refers to an anion having a single negative charge. As used herein, the term "polyanion" refers to an anion that is multiply charged or has an overall negative charge that is greater than −1 (e.g., −2 or −3, etc.), such as a dianion. As used herein, the term "monocation" refers to a cation having a single positive charge. As used herein, the term "polycation" refers to a cation that is multiply charged or has an overall positive charge that is greater than +1 (e.g., +2 or +3, etc.), such as a dication.

The term "conveyed gas" refers to a gas that is moving or flowing. For example, a conveyed gas may be conveyed by natural convection, forced convection, or a combination of these.

The term "ligand" is intended to be consistent with the term as would be recognized by one of skill in the fields of inorganic chemistry or coordination chemistry. Generally, a ligand is an atom, ion, functional group, or molecule that is chemically coordinated with one or more central atoms of a coordination complex. Generally, in a hexanuclear complex, a ligand is an atom, ion, functional group, or molecule that is chemically coordinated with one or more of the six metal atoms of the hexanuclear cluster, being a form of a coordination complex. A ligand may be ionic or may be neutral. Generally, but not necessarily, a ligand is a Lewis base and/or an electron-donor.

The term "metal oxide" refers to an oxide or oxidized compound or material characterized by a chemical formula which includes O and at least one metal element of the Periodic Table. The term "nonmetal oxide" refers to an oxide or oxidized compound or material characterized by a chemical formula which includes O and at least one nonmetal element and/or at least one metalloid element of the Periodic Table. Generally, but not necessarily, a nonmetal oxide is an oxide material characterized by a chemical formula that does not comprise a metal element. As used herein, the term "metalloid" refers to any of B, one or more allotropes of C (e.g., graphite, graphene, carbon black, carbon nanotubes, pyrolyzed carbon, graphitic carbon, graphitizable carbon, non-graphitizable carbon, etc.), Si, Ge, As, Sb, Te, Po, and At. Relevant nonmetal oxides include metalloid oxides such as $SiO_2$, $SiO_x$, $SiO_xC_y$, GeO, $GeO_2$, and $GeO_x$, where x and y are independently selected from the range of 0.1 and 2. An "oxide" refers to a solid state chemical compound that contains at least one oxygen atom and at least one other element in its chemical formula.

As used herein, the term "chemical bond" refers to any one or any combination of chemical bonds between chemical species, such as an ionic bond, a covalent bond, a coordinate bond (also referred to as coordinate covalent bond, a dipolar bond, and a dative bond), metallic bond, an intermolecular bond, such as a hydrogen bond and/or van der Waals forces, or any combination of these. The term "chemically bound" refers to species that interact with a chemical bond. A chemical species is a species that may be referred to as an atom, an ion, a molecule, a compound, or a chemical, for example. A species being "chemically coordinated" with another species refers to the interaction between the two species comprising a coordinate bond.

As used herein, the term "polymer" refers to a molecule composed of repeating structural units connected by covalent chemical bonds often characterized by a number of repeating units, also referred to as base units (e.g., greater than or equal to 5 base units). As used herein, a term "polymer is inclusive of" an "oligomer" (i.e., an oligomer is a polymer; i.e., a polymer is optionally an oligomer). The term "polymeric material" is more broadly inclusive of polymers as well as coordination polymers, having a plurality of repeating units, each repeating unit being a coordination complexes, such as, but not limited to, metal-organic frameworks and polypyridine complexes.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

The systems described herein are configured to employ hexanuclear clusters as photosensitizers for generating singlet oxygen, where the hexanuclear clusters are immobilized on a substrate, irradiated by light, and exposed to gas comprising molecular oxygen. The generated singlet oxygen can then inactivate pathogens in the gas and/or on a surface. Gas comprising triplet oxygen may be conveyed to the hexanuclear clusters. The generated singlet oxygen may be conveyed away from the hexanuclear clusters, optionally.

Hexanuclear clusters useful for the systems and embodiments disclosed herein include those described in literature cited throughout herein, including but not limited to the following references, each of which is incorporated herein in its entirety to the extend not inconsistent herewith: (1) D. Nocera, "Spectroscopy, Electrochemistry, and Photochemistry of Polynuclear Metal-Metal Bonded Complexes" 1984, Thesis, California Institute of Technology, DOI: 10.7907/T14G-4N32; (2); B. Kraut, et al., "Photochemical reactivity of the cluster tetradecachlorohexamolybdate(2-): photosubstitution and photoredox processes", Inorg. Chem. 1989, 28, 26, 4578-4583, DOI: 10.1021/ic00325a009; (3) A. W. Maverick, et al., "Spectroscopic, electrochemical, and photochemical properties of molybdenum(II) and tungsten(II) halide clusters", J. Am. Chem. Soc. 1983, 105, 7, 1878-1882, DOI: 10.1021/ja00345a034; (4) J. A. Jackson, et al., "Efficient Singlet Oxygen Generation from Polymers Derivatized with Hexanuclear Molybdenum Clusters", Chem. Mater. 1996, 8, 558-564, DOI: 10.1021/cm950443f; (6) J. A. Jackson, et al., "Oxygen quenching of electronically excited hexanuclear molybdenum and tungsten halide clusters", J. Phys. Chem. 1990, 94, 11, 4500-4507, DOI: 10.1021/j100374a029; (7) R. N. Ghosh, et al., "Fiber-optic oxygen sensor using molybdenum chloride cluster luminescence", Appl. Phys. Lett. 75, 2885 (1999), DOI 10.1063/1.125180; and (8) M. Strobele, et al., "The Synthesis and Luminescence of $W6Cl_{12}$ and $Mo_6Cl_{12}$ Revisited", Z. Anorg. Allg. Chem. 2009, 635, 822-827, doi: 10.1002/zaac.200801383. These references further include relevant synthetic protocols for making useful hexanuclear clusters and/or for immobilizing the hexanuclear clusters.

Figure 1:
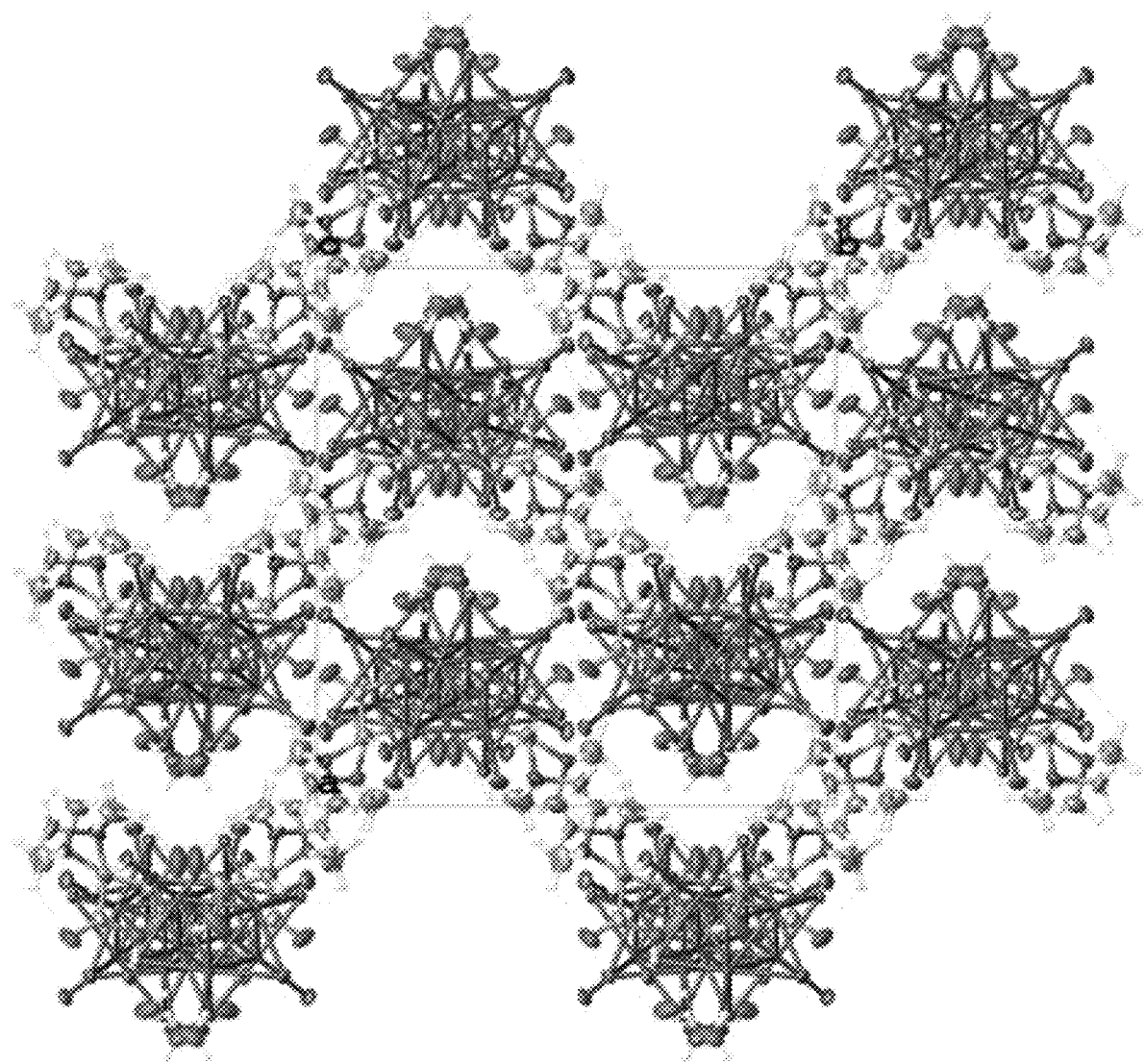
FIG. 1: A visual representation of $(Betaine-H)_2Mo_6Cl_{14}$, an example hexanuclear cluster according to embodiments disclosed herein.

The hexanuclear clusters useful herein are potent and robust singlet oxygen photosensitizers. The hexanuclear clusters disclosed herein include, for example, hexanuclear molybdenum clusters. For example, molybdenum(II) chloride clusters (e.g., FIG. 1) and salts thereof have been shown to act as high quantum efficiency photosensitizers for singlet oxygen specific reactions and are useful in aspects herein. The hexanuclear clusters are readily prepared and are activated by visible and/or near UV light. Furthermore, these clusters can be adsorbed onto inorganic oxide surfaces to increase surface area, thereby improving overall photocatalytic efficiency.

The deployment of gaseous singlet oxygen purification permits the sterilization of air within handling systems, thereby reducing bacterial and viral contamination. For example, there may be no mechanical barrier to gas compared to for solids or liquids.

The use of a disinfection methods on air systems allows for improvements in air safety especially with respect to airborne disease. Singlet oxygen decays (both temporally and with contact with metal surfaces) back to the triplet oxygen state of atmospheric oxygen, which is safe for breathing, thereby making the system useful for a much greater range of applications. In contact with moisture or other molecules, singlet oxygen likewise decays back to the triplet oxygen state, though the interaction with the molecules may involve oxidation or decomposition of those molecules. What is needed for the production of singlet oxygen in a functional device is a photocatalyst that efficiently produces singlet oxygen from ambient air and a readily available light source. Many methods for producing singlet oxygen involve either short wavelength ultraviolet light or organic sensitizers. UV light has health issues and the organic sensitizers have limited lifetimes. The use of an extremely stable molybdenum (II) chloride clusters that are activated at visible or near UV light provides exceptional advantages. The hexanuclear clusters disclosed herein are capable of being photosensitizers for generation of singlet oxygen upon exposure to light, for example, visible light, ultraviolet light, near infrared light, or any combination of these. The inorganic clusters can be absorbed on supports such as silica and mounted on screens for treatment of ambient air. Potential applications are for hospital settings and for purification of air entering a room from a central air conditioning that can result in cross contamination of workspaces. Systems disclosed herein include a mobile or handheld system that produces a stream of singlet oxygen for treatment of surfaces.

High intensity UV light can be used to decontaminate surfaces and air streams; however, the UV sources require considerable energy and can be a health hazard. Moreover, shadowing greatly diminishes UV exposure and therefore efficacy. An oxygen based alternative approach is sterilization with ozone, but this material has been shown to be ineffective, especially in the presence of biological contaminants including albumin. Additionally, the long lived byproducts of ozone sterilization can cause animal mortality between 4 and 10 ppm, within hours of exposure. In contrast, singlet oxygen has a short life time and decays over short distances. Moreover, the only byproduct of singlet oxygen's decay is non-toxic, ground state oxygen, making this a safer, more easily employable technology. For air sterilization a novel singlet oxygen technology may be the method of choice, because of its low cost and robustness of inorganic photosensitizers.

FIG. 3 provides a photograph (FIG. 3A, left) of an example system for generating singlet oxygen, according to aspects herein. In certain embodiments, the device is configured to direct or convey gas comprising singlet oxygen onto a surface for inactivating pathogens on or near the surface. In certain embodiments, the device is configured to inactivate airborne pathogens. Also shown is a schematic (FIG. 3B, right) of a system for generating singlet oxygen, according to aspects herein. In embodiments, the depicted system may be used for inactivation of airborne pathogens, in which embodiments features shown downstream of the photocatalysts, such as the sterilization target, may be optional. Embodiments disclosed herein include variations of the systems depicted here.

As shown in FIG. 3 the system of this embodiment comprises a light source, such as a visible light LED (light emitting diode) or array of LEDs, a photocatalyst, such as any of the hexanuclear clusters described herein optionally provide on or associated with a substrate, optionally a gas conveyor, such as one or more pumps, blowers, fans, compressors, fluid actuators, etc. for establishing a flow, transporting and/or mixing gas, and optionally an exit reactor for deactivating or removing singlet oxygen. As shown in FIG. 3, the system is configured such that light from the light source is provided to the photocatalyst, thereby activating the photocatalyst. In some embodiments, gas containing molecular oxygen ($O_2$), such as oxygen in the triplet state ($^3O_2$), is flowed into the system wherein it interacts with the photocatalyst, thereby generating singlet oxygen ($^1O_2$) in the gas. The gas comprising singlet oxygen is then transported to the sterilization target, wherein the singlet oxygen is available for inactivation of pathogens, such as pathogens on or near the surface of the sterilization target. Optionally, downstream of the sterilization target, the gas is exposed to an exit reactor for deactivating and/or removing at least a portion of, and optionally all of, any remaining singlet oxygen in the gas, for example, prior to leaving the system.

Figure 4:
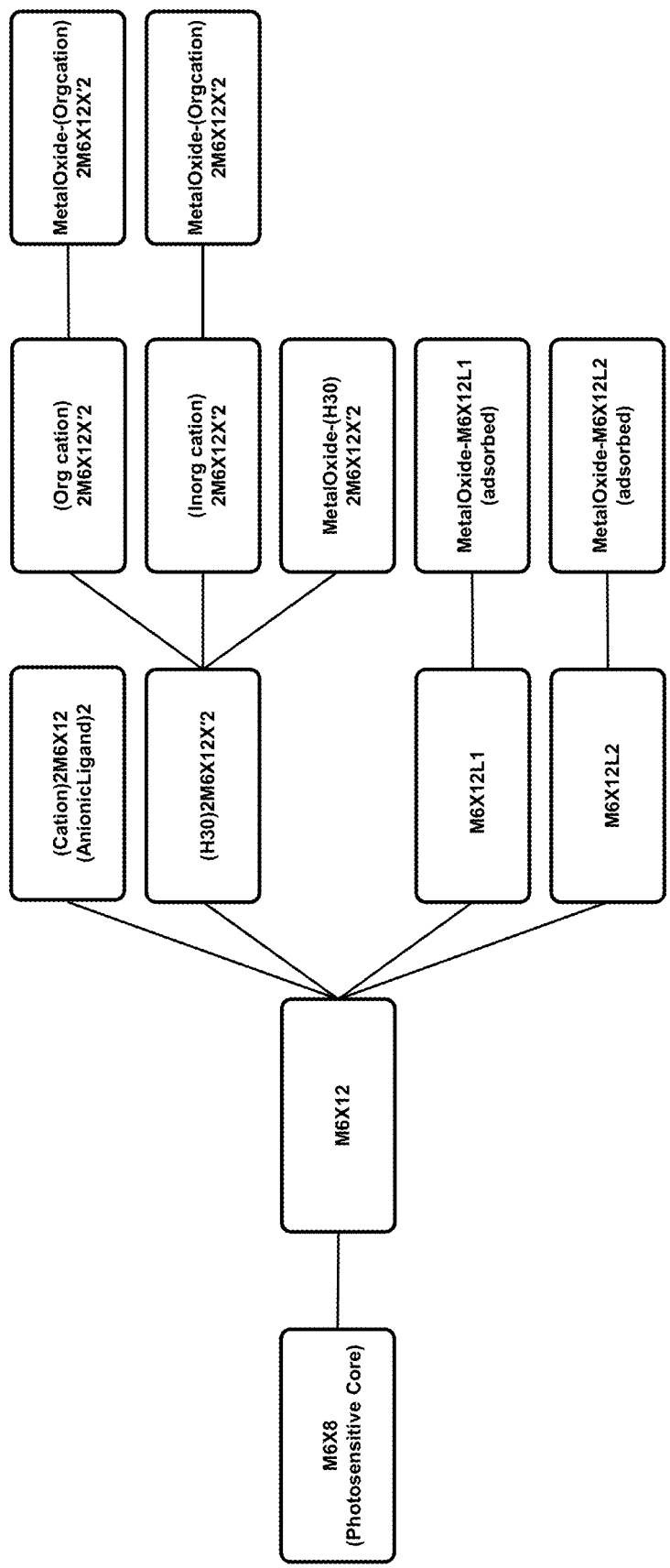
FIG. 4: A flow diagram of example chemical strategies for some embodiments of making, functionalizing and/or associating with substrates various embodiments of the hexanuclear complexes disclosed herein, included, but not limited to, steps such as salt exchanges and/or metal oxide impregnation/adsorption.

FIG. 4 provides a flow diagram of chemical strategies for some embodiments of making, functionalizing and/or associating with substrates various embodiments of the hexanuclear complexes disclosed herein, included, but not limited to, steps such as salt exchanges and/or metal oxide impregnation/adsorption. The chemical strategies in FIG. 4 are examples and, as will be understood by one of skill in the art, a wide range of approaches may be used for synthesizing, making, purifying and functionalizing the hexanuclear complexes disclosed herein, and for associating the hexanuclear complexes disclosed herein with substrates, including via non-covalent association, covalent association, physical association, linking, bonding, immobilization, crosslinking, physical distribution, surface deposition, impregnating, and the like.

Figure 5:
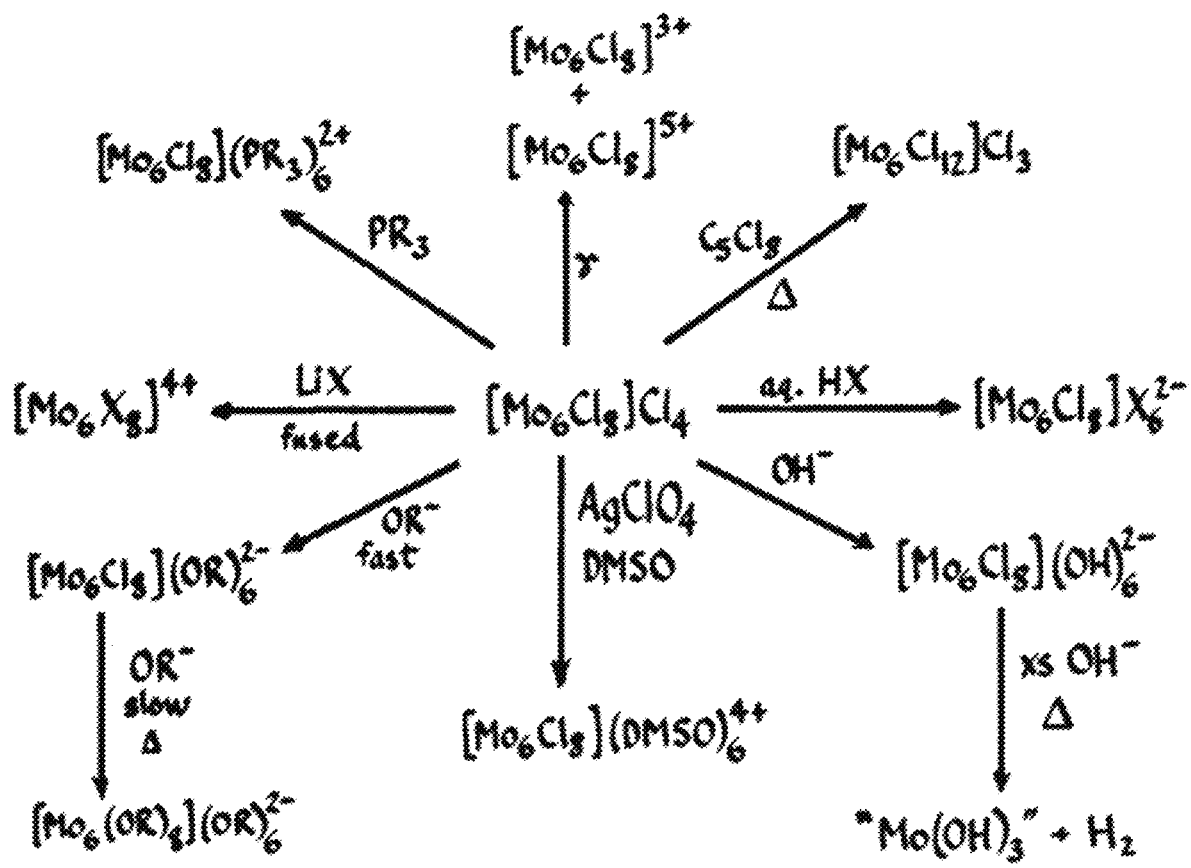
FIG. 5: A schematic showing example reactions schemes for $[Mo_6Cl_8]Cl_4$, an exemplary hexanuclear cluster disclosed herein, illustrating, for example, redox chemistry involved in formation of the cluster. This schematic and additional descriptions are found in A. W. Maverick (1982) ("Spectroscopy and Photochemistry of Polynuclear Metal Complexes," Dissertation (Ph.D.), California Institute of Technology, doi:10.7907/PBEA-8W62), which is incorporated herein by reference.

FIG. 5 provides a schematic showing example reactions schemes for [$Mo_6Cl_8$]$Cl_4$, an exemplary hexanuclear cluster disclosed herein, illustrating, for example, redox chemistry involved in formation of the cluster. This schematic and additional descriptions are found in A. W. Maverick (1982) ("Spectroscopy and Photochemistry of Polynuclear Metal Complexes," Dissertation (Ph.D.), California Institute of Technology, doi:10.7907/PBEA-8W62), which is incorporated herein by reference.

Various potentially useful descriptions, background information, applications of aspects herein, terminology (to the extent not inconsistent with the terms as defined herein), mechanisms, compositions, methods, synthetic protocols, definitions, and/or other embodiments may be found in the following references, each of which is incorporated herein in its entirety to the extent not inconsistent herewith:

1. DeRosa M C, Crutchley R J. Photosensitized singlet oxygen and its applications. *Coord Chem Rev.* 2002; 233-234:351-371. doi:10.1016/S0010-8545(02)00034-6
2. Jarvi M T, Patterson M S, Wilson B C. Insights into photodynamic therapy dosimetry: Simultaneous singlet oxygen luminescence and photosensitizer photobleaching measurements. *Biophys J.* 2012; 102(3):661-671. doi: 10.1016/j.bpj.2011.12.043
3. Bartusik D, Aebisher D, Lyons A M, Greer A. Bacterial inactivation by a singlet oxygen bubbler: identifying factors controlling the toxicity of (1)O2 bubbles. *Environ Sci Technol.* 2012; 46(21):12098-12104. doi:10.1021/es303645n
4. Bartusik D, Aebisher D, Ghafari B, Lyons A M, Greer A. Generating singlet oxygen bubbles: a new mechanism for gas-liquid oxidations in water. *Langmuir.* 2012; 28(5): 3053-3060. doi:10.1021/la204583v
5. Maisch T, Baier J, Franz B, et al. The role of singlet oxygen and oxygen concentration in photodynamic inactivation of bacteria. *Proc Natl Acad Sci USA.* 2007; 104(17):7223-7228. doi: 10.1073/pnas.0611328104
6. Maisch T, Eichner A, Spath A, et al. Fast and Effective Photodynamic Inactivation of Multiresistant Bacteria by Cationic Riboflavin Derivatives. *PLoS One.* 2014; 9(12): e111792. doi:10.1371/journal.pone.0111792
7. Jackson J A, Turro C, Newsham M D, Nocera D G. Oxygen quenching of electronically excited hexanuclear molybdenum and tungsten halide clusters. *J Phys Chem.* 1990; 94(30):4500-4507. doi:10.1021/j100374a029
8. Ströbele M, Jüstel T, Bettentrup H, Meyer H J. The synthesis and luminescence of $W_6Cl12$ and $Mo_6Cl_{12}$ revisited. *Zeitschrift fur Anorg and Allg Chemie.* 2009; 635(6-7):822-827. doi:10.1002/zaac.200801383
9. Silk& M, Ozer A Y. Sterilization Methods and the Comparison of E-Beam Sterilization with Gamma Radiation Sterilization. *FABAD J Pharm Sci.* 2009; 34(January 2016):43-53.
10. URATA M, ISOMOTO H, MURASE K, et al. Comparison of the Microbicidal Activities of Superoxidized and Ozonated Water in the Disinfection of Endoscopes. *J Int Med Res.* 2003; 31:299-306.

EXAMPLE 1

Figure 6:
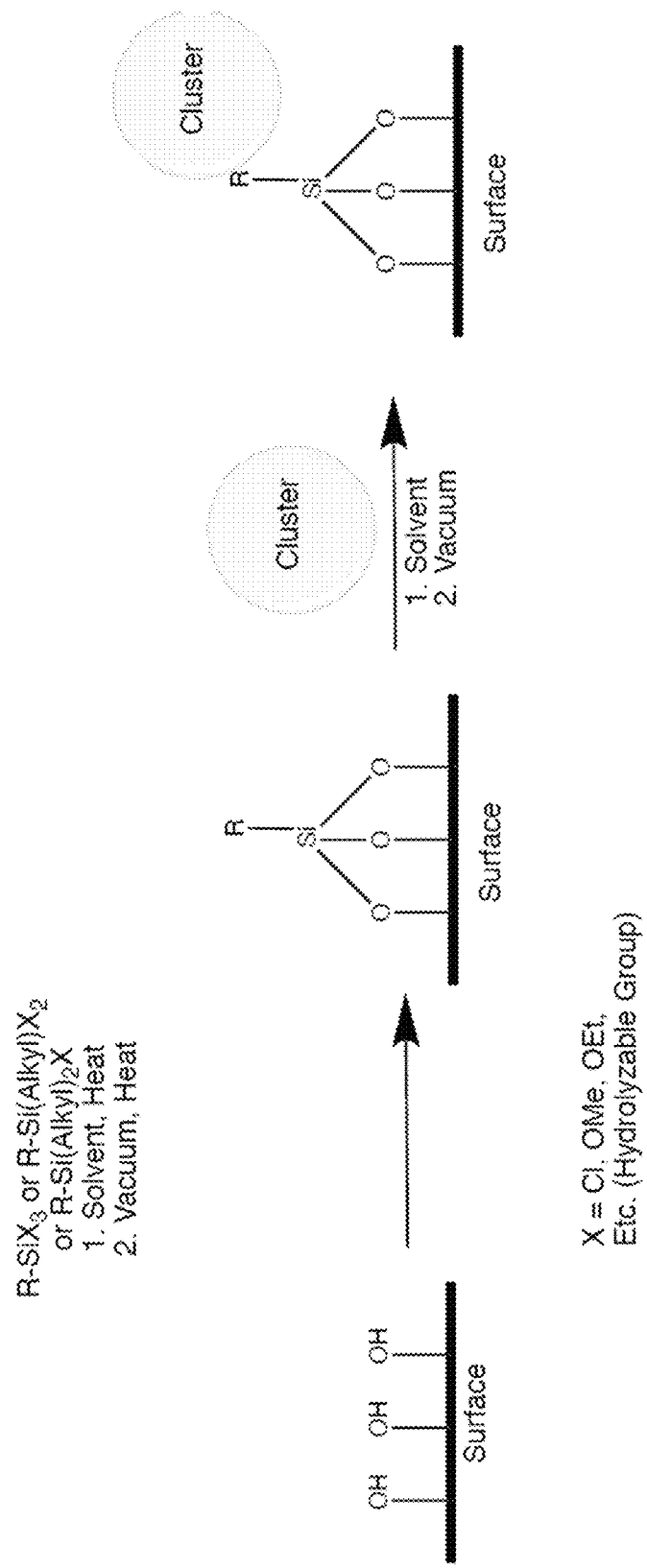
FIG. 6: Exemplary schematic depicting immobilization, according to various aspects herein, of hexanuclear clusters, according to various aspects herein, on a surface of a substrate. The schematic shows linking reagents bearing cationic, neutral, and/or anionic groups for coordination with hexanuclear clusters as a means of attachment. In particular, the immobilization schemes represented by FIG.

Substrate Processing and Schemes for Immobilization Hexanuclear Clusters on Different Substrates A schematic depicting association and/or immobilization, according to various aspects herein, of hexanuclear clusters, according to various aspects herein, on a surface of a substrate (e.g. external surface and/or surface of pores) is shown in FIG. 6. FIG. 6 shows linking reagents bearing cationic, neutral, and/or anionic groups for chemical association or coordination (or physical association) with hexanuclear clusters for attachment. In various aspects, the depicted "R" group(s) of the silane linker molecule or silane linker group represents one or more than one atom, ion, group, compound, or molecule that is chemically attached to the silane group and capable of directly or indirectly chemically attaching to one or more hexanuclear clusters, such as via a coordinate bond between the R group(s) and a hexanuclear cluster or between the R group(s) and ligand(s) of a hexanuclear cluster. Optionally, the silane molecule's or silane group's "R" group(s) is or comprises for example an organic or inorganic monocation, organic or inorganic dication, an organic or inorganic monoanion, an organic or inorganic dianion, or an organic or inorganic neutral Lewis base ligand which may coordinate with a hexanuclear cluster. Optionally, the silane molecule's or silane group's "R" group(s) is or comprises a linker group capable of coordinating with or attaching to an organic or inorganic monocation, organic or inorganic dication, an organic or inorganic monoanion, an organic or inorganic dianion, or an organic or inorganic neutral Lewis base ligand which may coordinate with a hexanuclear cluster. Optionally, the silane molecule's or silane group's "R" group(s) may charge-balance and coordinate with a cationic or anionic hexanuclear cluster such as in the case of the "R" group(s) being or comprising an organic or inorganic monocation, organic or inorganic dication, an organic or inorganic monoanion, or an organic or inorganic dianion. Optionally, one silane linker molecule or silane linker group is associated or attached to one hexanuclear cluster via the silane molecule's or silane group's R group(s). Optionally, one hexanuclear cluster may be associated with or attached to more than one silane linker molecules or silane linker groups via the "R" groups of the more than one silane linker molecules or silane linker groups. As an illustrative example, an anionic hexanuclear cluster (e.g., having formula $M_6X_8L_6$) may be immobilized on a substrate by coordinating with two silane molecules or silane groups via $NH_3^+$ groups, which may be depicted as: ($NH_3^+$-linker-Si-surface)$_2$($M_6X_8L_6$). As an illustrative example, a neutral hexanuclear cluster (e.g., having formula 6X8L4) may be immobilized on a substrate by coordinating with two silane molecules or silane groups via pyridine groups, which may be depicted as: (Py-linker-Si-surface)$_2$ ($M_6X_8L_4$). As an illustrative example, a hexanuclear cluster may be immobilized on a substrate by coordinating with two silane molecules or silane groups a scheme depicted as: $(Cation)_2Mo_6Cl_{12}(Anion^--linker-Si-surface)_2$.

FIG. 7 is a schematic depicting non-covalent immobilization, according to various aspects herein, of hexanuclear clusters, according to various aspects herein, on a surface of a substrate. The schematic shows immobilization of the clusters via adsorption to a surface, for example, via solution deposition and exposure to vacuum and/or heat.

In schemes represented by both FIGS. 6 and 7, the substrate surface may be any of a metal oxide, a nonmetal oxide, a metalloid oxide, a polymer, a coordination polymer or polymeric material, an organofluoride material, a fluoropolymer, an allotrope of carbon, or a combination of these.

Optionally, immobizilation of hexanuclear clusters may involve dissolution or suspension of the clusters in a suitable solvent, or solvent mixture, followed by deposition of the resulting solution on the substrate and evaporation of the solvent. Binding can be enhanced on substrates by incorporating ligands (neutral, cationic, or anionic) which interact directly with the cluster. The result may a chemical association or adsorption, which may be more significant in magnitude than a pure physical adsorption. The use of different charge states allow for modification of solubilities of the clusters. Based on application needs, this is a factor for immobilization and manufacture of systems disclosed herein.

A non-exhaustive listing of useful silane linker molecules and groups are provided in the catalogue of Gelest, Inc. titled "Silane Coupling Agents: Connecting Across Boundaries" 3rd Edition, Barry Arkles, 2014. The aforementioned catalogue publication is incorporated herein by reference.

EXAMPLE 2

Substrate Processing and Schemes for Immobilization Hexanuclear Clusters on Different Substrates This Example provides a non-exhausting listing of shorthand depictions of exemple schemes for immobilizing hexanuclear clusters on substrates for some embodiments:
  MetalOxide→MetalOxide-Silane-Amine→MetalOxide-Silane-CationicAmine→MetalOxide-Silane-CationicAmine-Cluster(2-)
  MetalOxide→MetalOxide-Silane-Organic→MetalOxide-Silane-OrganicCation→MetalOxide-Silane-Organic-Cation-Cluster(2-)
  MetalOxide→MetalOxide-Silane-NeutralLigand→MetalOxide-Silane-NeutralLigand-NeutralCluster(0)
  MetalOxide→MetalOxide-SilaneAnionicLIgand→MetalOxide-Silane-AnionicLigand-CationicCluster(2+)
  Polymer→Polymer-NeutralLigand→Polymer-NeutralLigand-NeutralCluster(0)
  Polymer→Polymer-AnionicLigand→Polymer-AnionicLigand-Cluster(2+)
  Polymer→Polymer-CationicLigand→Polymer-CationicLigand-Cluster(2-)

EXAMPLE 3

Substrate Processing and Schemes for Immobilization Hexanuclear Clusters on Different Substrates Surfaces bearing covalently attached cations, anions, cationic ligands, anionic ligands, and neutral ligands may be prepared for incorporating hexanuclear clusters for some embodiments.

Polymer:
  Cationic: Polyamines, Polypyridines (acidified), etc.
  Anionic: Polycarboxylic acids, etc.
  Neutral: Polypyridines, etc.
  Metal oxides/Metaloid oxides (ie, $TiO_2$, $Fe_2O_2$, $SiO_2$, etc.) (examples are included in gelest catalogue sent months prior):
  Cationic: silanes bearing cationic species grafted to the surface
  Anionic: silanes bearing anionic species grafted to the surface
  Neutral: silanes bearing neutral ligands grafted to the surface
  Materials can be neutrally chemisorbed (dissolved, applied, and dried on a surface)—water soluble ligands for water deposition or organic ligands for organic deposition.

EXAMPLE 4

Synthesis of Hexanuclear Clusters

This Example provides examples pertaining to a non-exhausting set of protocols involved in preparing certain exemplary hexanuclear clusters of some embodiments.

H2Mo6Cl4 type structures: Mo6Cl12 is treated with hot HCl under stirring. Following cooling, the crystals are filtered, washed with deionized water, and dried under vacuum to afford H2Mo6Cl14

(Organic Cation)2Mo6Cl14 type structures: H2Mo6Cl14 is dissolved in warm HCl solution. To this solution is added an excess of (Organic Cation)Cl. The solution is cooled and crystals precipitate. Precipitated crystals are washed with deionized water and dried under vacuum to afford (Organic Cation)Mo6Cl14

(Organic Cation)2Mo6Cl12X2 type structures: H2Mo6Cl14 is dissolved in warm HCl solution. To this solution is added an excess of (Organic Cation)X. The solution is cooled and crystals precipitate. Precipitated crystals are washed with deionized water and dried under vacuum to afford (Organic Cation)2Mo6Cl12X2

(Organic Dication)Mo6Cl14 type structures: H2Mo6Cl14 is dissolved in warm HCl solution. To this solution is added an excess of (Organic Dication)Cl. The solution is cooled and crystals precipitate. Precipitated crystals are washed with deionized water and dried under vacuum to afford (Organic Dication)Mo6Cl14

(Organic Dication)Mo6Cl14 type structures: H2Mo6Cl14 is dissolved in warm HCl solution. To this solution is added an excess of (Organic Dication)X. The solution is cooled and crystals precipitate. Precipitated crystals are washed with deionized water and dried under vacuum to afford (Organic Dication)Mo6ClX2

(Cation)2Mo6Cl12X2 type structures: H2Mo6Cl14 is dissolved in warm HCl solution. To this solution is added an excess of (Cation)X. The solution is cooled and crystals precipitate. Precipitated crystals are washed with deionized water and dried under vacuum to afford (Organic Cation)2Mo6Cl12X2

(Dication)Mo6Cl14 type structures: H2Mo6Cl14 is dissolved in warm HCl solution. To this solution is added an excess of (Dication)X. The solution is cooled and crystals precipitate. Precipitated crystals are washed with deionized water and dried under vacuum to afford (Dication)Mo6ClX2

H2Mo6Cl12X2 type structures: Mo6Cl12 is treated with hot HX under stirring. Following cooling, the crystals are filtered, washed with deionized water, and dried under vacuum to afford H2Mo6Cl12X2

H2Mo6Cl14 is treated with hot HX under stirring. Following cooling, the crystals are filtered, washed with deionized water, and dried under vacuum to afford H2Mo6Cl12X2

Neutral Mo6Cl12 from H2Mo6Cl14: H2Mo6Cl14 is heated under vacuum to evaporate evolve gaseous acid to afford Mo6Cl12

Neutral Mo6Cl12 from H2Mo6Cl12X2: H2Mo6Cl12X2 is heated under vacuum to evaporate gaseous HX (must be volatile) to afford Mo6Cl12

EXAMPLE 5

System Configurations and Useful Parameters

FIG. 8 is a schematic depicting select features or aspects of an exemplary system for generating singlet oxygen, according to various aspects disclosed herein. As shown in FIG. 8, a first surface (or surfaces) having photocatalyst is exposed to light from a first light source and/or a second light source, such as visible light LED light sources including LED arrays, for activating the photocatalyst on the first surface. Gas comprising triplet $O_2$ is transported to the system where it interacts with photocatalyst, thereby generating singlet $O_2$ in the gas. The gas comprising triplet $O_2$ and singlet $O_2$ is transported into contact with a second surface (or surfaces) having photocatalyst which is also exposed to light from the first light source and/or a second light source, thereby further generating singlet $O_2$ in the gas, which may enrich the amount of singlet $O_2$ in the gas. In the embodiment shown in FIG. 8, the gas comprising singlet $O_2$ may be used for inactivation of pathogens in the gas itself or may be used for inactivation of pathogens on or near a surface that is contacted with the gas comprising singlet $O_2$, for example, by transport of the gas containing singlet $O_2$ to the surface.

FIG. 9 is an illustration of a generalized system, according to various aspects disclosed herein, for generating singlet oxygen. FIG. 9 shows system 100 for generating singlet oxygen. System 100 comprises photosensitizing component 110. Photosensitizing component 110 comprises substrate 112 and hexanuclear clusters 114 immobilized, such as via chemical association or physical association, on at least a portion of substrate 112, such as one or more external surfaces and/or surfaces of pores. System 100 comprises one or more light sources 120 in optical communication with photosensitizing component 110. In some embodiments, light sources are internal to system 100 as depicted in FIG. 9, such as via internal lamps, LEDs, lasers, and arrays thereof. Optionally, light source 120 is external to or otherwise provided not as part of system 100, such as in the case of light source 120 being solar irradiation. Light source 120 provides light 122, optionally visible light, to photosensitizing component 110, for example, providing wavelengths, energies and/or powers sufficient to provide activation of photosensitizing component 110.

System 100 optionally comprises a gas conveyor (165), such as but not limited to one or more fans, one or more blowers, one or more compressors, one or more pumps, one or more fluid actuators or a combination of these for transporting the gas to the clusters and/or from the clusters and/or for mixing the gas within the system 100, such as by turbulently mixing the gas. Feed gas 102 is provided to system 100. Feed gas 102 comprises molecular oxygen. Feed gas 102 optionally comprises pathogens 140. Feed gas 102 may be conveyed to, toward, or into photosensitizing component 110. Gas leaving photosensitizing component is conveyed gas 104. Conveyed gas 104 comprises singlet oxygen. Conveyed gas is optionally free of pathogens 140 or has a reduced concentration of pathogens 140 compared to feed gas 102.

Exit gas 106 exits or is conveyed out of system 100. Exit gas 106 comprises triplet oxygen. Exit gas 106 is optionally free of singlet oxygen. Exit gas 106 is preferably, but not necessarily, free of pathogens 140 or has a reduced concentration of pathogens 140 compared to feed gas 102. Optional system 100 further comprises exit reactor 155 for inactivating and/or removing at least portion, and optional all, of singlet oxygen from exit gas 106. Optionally for some embodiments, conveyed gas 104 comprising singlet oxygen may be directed to surface 130, for inactivation of pathogens on or near surface 130.

System 100 may configured to provide for inactivation of pathogens in feed gas 102, for example, comprising air, for example air for use in a sterile or otherwise clean environment. System 100 may be configured as a portable unit provided in an enclosure (e.g. a room), wherein gas (e.g. air) from the enclosure is passed through the system for inactivation of pathogens therein, and optionally recirculated into the enclosure.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX—YY" (wherein XX and YY refer to claim numbers) is intended to provide a multiple dependent claim in the alternative form, and in some embodiments is interchangeable with the expression "as in any one of claims XX—YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every device, system, formulation, combination of components, or method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A system for generating singlet oxygen in a gas, the system comprising:
a substrate; and
hexanuclear clusters operably immobilized on at least a portion of the substrate;
wherein each of the hexanuclear clusters comprises a photosensitive octahedral core complex characterized by formula FX1a:

$$M_6X_8 \hspace{4cm} (FX1a);$$

wherein each M is W;
wherein each X is independently a halide anion ligand;
wherein the hexanuclear clusters are exposed to the gas and the gas comprises at least $O_2$ gas;
wherein the hexanuclear clusters are exposed to a light;
wherein each of the hexanuclear clusters is a photosensitizer configured to generate the gaseous singlet oxygen when irradiated by the light in the presence of the $O_2$ gas; and
wherein the hexanuclear clusters are immobilized on the surface of the substrate via non-covalent association between the hexanuclear clusters and silane linker groups, the silane linker groups being covalently attached to the surface of the substrate.

2. The system of claim 1, wherein each of the hexanuclear clusters is independently neutral, cationic, or anionic; wherein each of the cationic clusters, if present, is charge-balanced with one or more counterions; and wherein each of the anionic clusters, if present, is charge-balanced with one or more counterions.

3. The system of claim 1, wherein each of the hexanuclear clusters is independently characterized by formula FX2a, FX2b, or FX2c:

$$M_6X_8L_6 \quad (FX2a);$$

$$M_6X_8L_4 \quad (FX2b); \text{ or}$$

$$M_6X_8L_2 \quad (FX2c); \text{ wherein:}$$

each M is W;
each X is independently a halide anion ligand; and
each L is independently an organic or inorganic monoanion ligand.

4. The system of claim 3, wherein each L is independently Cl, Br, I, C, or O.

5. The system of claim 1, wherein each of the hexanuclear clusters is independently characterized by formula FX2d, FX2e, or FX2f:

$$M_6X_8(L')^{6-} \quad (FX2d);$$

$$M_6X_8(L')^{4-} \quad (FX2e); \text{ or}$$

$$M_6X_8(L')^{2-} \quad (FX2f); \text{ wherein:}$$

each M is independently W;
each X is independently a halide anion ligand; and
each L' is independently one or more organic or inorganic monoanion and/or polyanion ligands.

6. The system of claim 1, wherein each of at least a fraction of the hexanuclear clusters is independently a compound characterized by formula FX3a, FX3b, or FX3c:

$$(M_6X_6L_6)^{2-}(A^C)_p^{2+} \quad (FX3a);$$

$$(M_6X_8L_4)(A^N)_n \quad (FX3b); \text{ or}$$

$$(M_6X_8L_2)^{2+}(A^A)_m^{2-} \quad (FX3c); \text{ wherein:}$$

each M is independently W;
each X is independently a halide anion ligand;
each L is independently an organic or inorganic monoanion;
p is 2 and each $A^C$ is independently a counterion being an organic or inorganic monocation or p is 1 and $A^C$ is a counterion being an organic or inorganic dication;
m is 2 and each $A^A$ is independently a counterion being an organic or inorganic monoanion or m is 1 and $A^A$ is a counterion being an organic or inorganic dianion; and
n is an integer selected from the range of 1 to 2 and $A^N$ is an organic or inorganic neutral Lewis base ligand.

7. The system of claim 6, wherein each $A^N$ is independently selected from the group consisting of N, a substituted or unsubstituted pyridine, a substituted or unsubstituted amine, a substituted or unsubstituted methide, carbon monoxide, a substituted or unsubstituted triphenylphosphine, a substituted or unsubstituted triphenylarsine, a substituted or unsubstituted dimethylsulfide, a substituted or unsubstituted diemthylselenide, ammonia, and any combination thereof; and wherein each $A^C$ is independently selected from the group consisting of a metal monocation, $NH_4^+$, tetrabutylammonium, tetramethylammonium, tetraethylammonium and any combination thereof.

8. The system of claim 1, wherein each of the hexanuclear clusters comprises a composition characterized by formula FX4:

$$M_6X_{12} \quad (FX4); \text{ wherein:}$$

each M is independently W; and
each X is independently a halide anion.

9. The system of claim 1, wherein each X is Cl, Br, or I.

10. The system of claim 1, wherein the substrate has a composition characterized as a metal oxide, nonmetal oxide, a polymer, a coordination polymer or polymeric material, an organofluoride material, an allotrope of carbon, or a combination of these.

11. The system of claim 1, wherein the substrate comprises a plurality of carbon-fluoride bonds.

12. The system of claim 1, wherein the substrate comprises metal oxide or non-metal oxide particles having the clusters operably connected or associated thereto.

13. The system of claim 1, wherein the light comprises visible light, ultraviolet light, or any combination of these.

14. The system of claim 1 comprising one or more fans, one or more blowers, one or more compressors, one or more pumps, one or more fluid actuators or a combination of these for conveying the gas to the clusters and/or from the clusters.

15. The system of claim 1, wherein the gas is air.

16. The system of claim 1, wherein the system is integrated with an HVAC system, a room air circulation system, an air filtration system, a medical facility air cleaning system, a clean-room air cleaning system, a utensil disinfection system, or any combination of these.

17. The system of claim 1, wherein each of the hexanuclear clusters includes monoatomic and/or polyatomic ligands coordinated with or bound to the metal atoms of the cluster.

18. The system of claim 1, wherein each of the hexanuclear clusters is independently characterized by formula FX2g:

$$M_6X_8(L') \quad (FX2g); \text{ wherein:}$$

each M is independently W;
each X is independently a halide anion ligand; and
each L' is independently one or more organic or inorganic monoanion and/or polyanion ligands.

19. A system for inactivation of pathogens via singlet oxygen, the system comprising:
a photosensitizing component for generating gaseous singlet oxygen, comprising:
  a substrate; and
  hexanuclear clusters operably immobilized on the substrate;
  wherein each of the hexanuclear clusters comprises a photosensitive octahedral core complex characterized by formula FX1a:

$$M_6X_8 \quad (FX1a);$$

wherein each M is W; and
  wherein each X is independently a halide anion;
a conveyed gas in gas-communication with the photosensitizing component;
  wherein the hexanuclear clusters are exposed to the gas and the gas comprises at least $O_2$ gas;
a light source configured to emit a light onto the hexanuclear clusters, the light being capable of photoactivating the hexanuclear clusters;
wherein each of the hexanuclear clusters is a photosensitizer configured to generate the gaseous singlet oxygen when irradiated by the light in the presence of the $O_2$ gas; and
wherein the hexanuclear clusters are immobilized on the surface of the substrate via non-covalent association between the hexanuclear clusters and silane linker groups, the silane linker groups being covalently attached to the surface of the substrate.

20. The system of claim 19 being a system for inactivation of airborne pathogens or a system for inactivation of pathogens on a surface, wherein:
- the conveyed gas comprises the airborne pathogens to inactivate the airborne pathogens in the gas via the gaseous singlet oxygen; or
- the conveyed gas, having the generated gaseous singlet oxygen, flows from the photosensitizing component onto the surface and the conveyed gas comprises the generated gaseous singlet oxygen at the surface.

21. A method for generating gaseous singlet oxygen in a gas, the method comprising:
- exposing hexanuclear clusters to the gas comprising at least O2 gas; and
- irradiating the hexanuclear clusters with a light;

wherein:
- each of the hexanuclear cluster is a photosensitizer configured to generate the gaseous singlet oxygen when irradiated by the light in the presence of the $O_2$ gas;
- the hexanuclear clusters are operably immobilized on at least a portion of a substrate;
- each of the hexanuclear clusters comprises a photosensitive octahedral core complex characterized by formula FX1a:

$$M_6X_8 \tag{FX1a};$$

wherein each M is W;

wherein each X is independently a halide anion ligand; and wherein the hexanuclear clusters are immobilized on the surface of the substrate via non-covalent association between the hexanuclear clusters and silane linker groups, the silane linker groups being covalently attached to the surface of the substrate.

* * * * *

UNITED STATES PATENT AND TRADEMARK OFFICE
CERTIFICATE OF CORRECTION

| | | |
|---|---|---|
| PATENT NO. | : 12,343,455 B2 | Page 1 of 1 |
| APPLICATION NO. | : 17/524654 | |
| DATED | : July 1, 2025 | |
| INVENTOR(S) | : Grubbs et al. | |

It is certified that error appears in the above-identified patent and that said Letters Patent is hereby corrected as shown below:

In the Claims

In Claim 6, Column 21, Line 31, in Formula (FX3a), please delete the term "$(M_6X_6L_6)^{2-}(A^C)_p^{2+}$" and replace with --$(M_6X_8L_6)^{2-}(A^C)_p^{2+}$--

Signed and Sealed this
Twenty-sixth Day of August, 2025

Coke Morgan Stewart
*Acting Director of the United States Patent and Trademark Office*